United States Patent [19]

Heller et al.

[11] 4,304,767
[45] Dec. 8, 1981

[54] POLYMERS OF DI- (AND HIGHER FUNCTIONALITY) KETENE ACETALS AND POLYOLS

[75] Inventors: Jorge Heller, Palo Alto; Robert F. Helwing, Sunnyvale; Donald W. Penhale, Cupertino, all of Calif.

[73] Assignee: SRI International, Menlo Park, Calif.

[21] Appl. No.: 150,052

[22] Filed: May 15, 1980

[51] Int. Cl.$^3$ .................... A61K 9/22; A61K 31/765; C08G 65/28
[52] U.S. Cl. .................................... 424/78; 128/260; 424/19; 424/22; 260/340.5 R; 260/340.7; 260/340.9 R; 260/338; 528/392
[58] Field of Search .................... 528/392; 260/340.7, 260/340.9, 340.5 R, 338; 424/78

[56] References Cited

U.S. PATENT DOCUMENTS

| | | | |
|---|---|---|---|
| 2,687,407 | 8/1954 | Orth | 528/392 |
| 2,909,506 | 10/1959 | Guest et al. | 528/392 X |
| 2,957,856 | 10/1960 | Guest et al. | 528/392 X |
| 3,087,918 | 4/1963 | Guest et al. | 528/392 |
| 4,136,252 | 1/1979 | Capozza | 528/392 X |
| 4,180,646 | 12/1979 | Choi et al. | 528/392 X |

*Primary Examiner*—Earl A. Nielsen
*Attorney, Agent, or Firm*—Edward B. Gregg; Donovan J. DeWitt

[57] ABSTRACT

This invention concerns ortho ester polymers having repeating mer units represented by the general formulas:

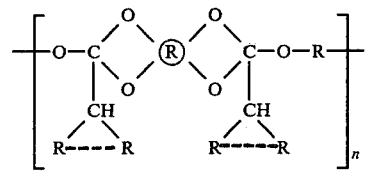

and

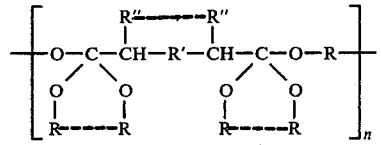

The polymers are formed by a condensation reaction between ketene acetals having a functionality of two or more and hydroxyl containing compounds having a functionality of two or more. Unlike most conventional condensation reactions, the reaction between a ketene acetal and an alcohol proceeds without the evolution of small molecule by-products which must be removed by distillation in order to achieve high molecular weight. Hence, this new process produces high molecular weight poly (ortho esters) in short reaction times, at essentially room temperature and at atmospheric pressure. Furthermore, linear thermoplastic materials are produced when both the ketene acetal and alcohol have functionalities of two; and because no volatile materials are produced, void free, thermoset materials are produced when either or both the alcohol and ketene acetal have functionalities greater than two and crosslinking occurs. The polymers are bioerodible and are useful in the fabrication of devices and coatings for delivering beneficial agents.

30 Claims, 2 Drawing Figures

Fig_1

Fig_2

POLYMERS OF DI- (AND HIGHER FUNCTIONALITY) KETENE ACETALS AND POLYOLS

The invention disclosure described herein was made in the course of or under National Institutes of Health Contract No. 1-HD-7-2826 with the U.S. Department of Health, Education and Welfare.

This invention relates to polymers which are bioerodible and are suitable as carriers or matrices for drugs and other beneficial agents used for therapeutic purposes and which, upon contact with the environment in which they are used, degrade and release the drug or other biologically active agent. The invention also relates to methods of preparing such polymers, to compositions of matter comprising the polymer and biologically active agents and to fabricated articles such as implants in which the polymer constitutes the matrix and contains a biologically active material.

There are available drug delivery devices such as those described in U.S. Pat. No. 4,069,307 in which a drug is included in a polymeric matrix from which it diffuses. There are also drug delivery devices in which a drug is contained in a capsule the walls of which are permeable to water and which, upon infusion of water, generate an internal osmotic pressure such as to force the drug through an orifice. Both types are implanted and require subsequent removal.

Another approach to drug delivery devices is typified by Choi and Heller U.S. Pat. No. 4,093,709, which employs a bioerodible polymer in which a drug is incorporated and which undergoes degradation (called bioerosion) to release the drug. Provided the degradation products are harmless, such an implant has the advantage that it does not require removal. The bioerodible polymers of that patent are poly (ortho esters) or polycarbonates.

A typical example of such a polymer and its method of synthesis is given in Example 1 of the Choi and Heller Patent and is a polymer prepared from trans-1,4-cyclohexane dicarbinol and 2,2-diethoxytetrahydrofuran. The polymer has the formula wherein n is an integer from 10 to 1000. As described in Example 1, of the Choi and Heller Patent this polymer is prepared by heating a mixture of the monomers and polyphosphoric acid, first at 110°–115° C. for 1½ to 2 hours with slow distillation of any liquid formed, then at 0.01 millimeter of mercury while the temperature is slowly increased to 180° C. The reaction is allowed to continue at 180° C. for 24 hours.

There are several disadvantages to this procedure which are typical of a transesterification reaction and to the polymeric end-products resulting therefrom, among which are the following:

The reaction takes a considerable period of time, in this particular instance in excess of 24 hours. Furthermore, it is necessary to remove by distillation under high vacuum the volatile products formed as a result of condensation. The necessity to remove the volatile material precludes formation of nonporous, dense crosslinked products obtained by using alcohols having functionalities greater than two.

A further disadvantage of this procedure is the difficulty in achieving very high molecular weights. It is well known that typical polymers prepared by condensation reactions involving a transesterification reaction have molecular weights of about 30,000. Since this is an average molecular weight, it is apparent that the product contains a considerable proportion of polymer of much lower molecular weight. In many instances the presence of low molecular weight polymer chains adversely affects mechanical properties.

A yet further disadvantage is the fact that a transesterification reaction is an equilibrium reaction which is driven to high polymer molecular weight by removal of a volatile by-product with a consequent shift of equilibrium. However, it is usually not possible to completely remove the diol by-product and varying amounts of this diol are very often found in the final polymer product.

Still another disadvantage is the fact that because of the high reaction temperatures and long reaction times, side-reactions can occur and the product is usually not pure because extraneous linkages can be formed.

Yet another disadvantage is due to the propensity of diols having fewer than five carbon atoms to form monomeric spiro structures which then need to be polymerized in a separate step.

The foregoing disadvantages are typical of bioerodible polymers prepared by condensation of monomers which have been patented heretofore.

It is an object of the present invention to provide improvements upon bioerodible polymers suitable for use as matrices for drugs and other beneficial agents.

More particularly it is an object of the present invention to provide a bioerodible polymer which is useful for such purposes and which can be made by an improved process having few or none of the aforementioned disadvantages.

A particular object is to provide polymers which can be made by a process which proceeds rapidly at low temperatures, usually below 40° C., without the evolution of any by-products. Therefore, either linear or dense, crosslinked matrices can be readily produced.

Another particular object is to provide a process of polymerization which is not an equilibrium reaction and whereby molecular weights as high as 200,000 can be routinely achieved.

Another object is to provide polymer structures having no significant amounts of unreacted monomers or extraneous linkages.

A further object is to provide a process in which there is no limitation on the number of carbon atoms in the diol whereby polyols having fewer than five carbon atoms may be employed, and such diols do not form monomeric spiro structures.

The above and other objects of the invention will be apparent from the ensuing description and the appended claims.

In accordance with the present invention, a ketene acetal having a functionality of two or more is reacted with a polyol, which term includes alcohols and phenols.

By "functionality" as applied to a ketene acetal is meant the ketene acetal group Thus a diketene acetal has a functionality of two, a triketene acetal has a functionality of three, etc. Similarly where the term "functionality" is used in connection with a polyol, it refers to the hydroxyl groups.

Such polymers have a number of advantages as matrices or carriers for drugs as explained below.

The monomeric polyols can be represented generally by the formula $$\underset{(OH)_y}{\overset{|}{HOROH}}$$

wherein y is zero or a positive integer. These are described below.

The monomeric ketene acetals are of two types as follows:

Type I Monomers wherein the terminal R groups are the same or different, and can be H or essentially hydrocarbon groups, primarily alkyl, aryl, cycloaliphatic or aralkyl groups, and may be saturated or unsaturated, and R is a quadrivalent grouping or atom.

The grouping may be a spiro structure or it may be a non-spiro grouping. A subgroup of Type I monomer is exemplified by Compounds XIII through XVIII in Table II below.

By "essentially hydrocarbon" is meant that the groups R may contain hetero atoms provided they do not inhibit polymerization with a polyol to an unacceptable degree, do not inhibit degradation of the polymer to an unacceptable degree and do not give rise to toxic or difficultly metabolizable degradation products. The formulation R—R indicates that the two R groups may be joined together to form a cyclic group or may be separate, unconnected groups.

Type II Monomers

Wherein the terminal R groups are the same or different essentially hydrocarbon groups, the R' groups are hydrogen or essentially hydrocarbon groups (defined as above) and R" is a bivalent organic grouping which is also essentially hydrocarbon (similarly defined).

The Type I monomers condense with diols HO—R—OH, R being an essentially hydrocarbon (similarly defined) bivalent group to produce linear polymers as follows:

wherein R is derived from the polyol and n is an integer greater than one and usually 100 to 300 or greater.

The Type II monomers polymerize with diols HO—R—OH (defined as above) to produce linear polymers as follows:

R and n are similarly defined.

It will be understood that where the polyol and/or the ketene acetal has or have functionalities greater than two, crosslinked polymers will result. As noted below crosslinking may also be achieved by other crosslinking agents.

Certain of the diketene acetals which can be used in the present invention are described in the literature, among which are the following:

Type I Diketene Acetals

This compound and its synthesis are described in Yasnitskii et al in Zhurnal obshchei Khimii 34, 1940–45 (1964).

Type II Ketene Acetals (R = methyl, ethyl, n-butyl, $CH_3-\underset{\underset{CH_3}{|}}{CH}-CH_2-$)

Scheeren and Aben, Tetrahedron Letters, 12, 1019–1020 (1974)

Scheeren et al., J. Royal Netherlands Chemical Society, 94, 196–8 (1975). The centrally located double bond may be employed to bring about crosslinking of linear ketene-diol polymers. Suitable crosslinking agents for this prupose are free radical type crosslinking agents such as benzoyl peroxide.

Methods of preparation of other polyfunctional ketene acetals which are not described in the literature and are believed to be novel are described in the examples below. Examples of such ketene acetals and general methods of synthesis are as follows:

The condensation of a glycol with diethylbromoacetals is described by R. M. Roberts, J. Corse, R. Boschaw, D. Seymour and S. Winstein in J. Am. Chem. Soc. 80, 1247–1254 (1958) and the dehydrohalogenation by F. Beyerstedt and S. M. McElvain in J. Am. Chem. Soc. 58, 529–53 (1936). Isomerization of the double bond has been described by E. J. Corey and J. W. Suggs in J. Org. Chem. 38, 3224 (1973).

These is another, somewhat less satisfactory method which involves an imino ether hydrochloride intermediate.

The reaction of imino ether hydrochlorides with diols has been described by S. M. McElvain and C. C. Aldridge in J. Am. Chem. Soc. 75, 3993–3396 (1975). The dealcoholation has been described by S. M. McElvain and J. T. Venerable in J. Am. Chem. Soc. 72, 1661–1669 (1950).

The procedures thus described in the cited literature may be adapted to synthesize the diketene acetals set forth above and below.

The addition of monohydric alcohols to mono ketene acetals has been intensely studied and described in the literature by McElvain and co-workers, in J. Am. Chem. Soc. commencing in 1936, e.g. Beyerstedt and McElvain, J.A.C.S. 58, 529 (1936), McElvain and Weyna J.A.C.S. 81, 2579 (1979) and in many papers in the same Journal between those dates. Most of these studies involve the addition of a monohydric alcohol to a mono ketene acetal. Scheeren and Aben, Tetrahedron Letters 12, 1019–1020 (1974) describe the addition of several monohydric alcohols to diketene acetals; see above. No description of polymers of polyols and polyfunctional ketene acetals is known and such are believed to be broadly novel.

Exemplary polyols suitable as reactants include diols, triols and the like that can enter into the polymerization reaction without adversely effecting it or the polymeric product. The polyols are known to the art in reported synthesis and they are commercially available. Generally, they include α,ω-aliphatic diols, triols and the like of the straight or branched chain type. Representative polyols are alkane polyols having a terminal hydroxyl group at the terminus of an alkylene chain of the formula wherein R is an alkylene chain of 2 to 12 carbon atoms and y is 0 to 6. Typical diols, named as the glycols, include 1,5-pentylene glycols; 1,6-hexylene glycol; 1,7-heptylene glycol; 1,9-nonylene glycol; 2,3-dimethyl-1,6-hexylene glycol; 3,6-diethyl-1,9-nonylene glycol; 1,12-dodecamethylene glycol; and the like.

Polyols containing more than 2 reactive hydroxyl radicals suitable for use herein include polyhydroxyl compounds such as 1,2,3,4,5,6-hexanehexol; 1,2,3-propanetriol; 1,2,5-pentanetriol; 1,3,5-pentanetriol; 1,2,4-butanetriol; 2-methyl-1,2,3-propanetriol; 2-methyl-2(hydroxymethyl) 1,2-propanediol; 1,4,7-heptanetriol; 1,5,10-decanetriol; 1,5,12-dodecanetriol; and the like.

Other polyols suitable for synthesizing the polymers include polyglycols containing a repeating glycol monoether moiety —OCH$_2$(CH$_2$)$_p$OH wherein p is 1 to 5, and the polyglycols are diglycols, triglycols, tetraglycols, and the like. Typical polyglycols include diethylene glycol, triethylene glycol, tetraethylene glycol, bis(4-hydroxybutyl)ether, bis(3-hydroxypropyl)ether, and the like.

Additional polyols that can be used in accordance with the invention are polyhydroxyl compounds having 2 or more reactive hydroxyl groups such as pentaerythritol; dipentaerythritol; β-methylglycerol; 1,4-cyclohexane dicarbinol in the cis, trans isomeric configuration or mixtures thereof; 2,2,4,4-tetramethyl cyclobutane 1,3-diol; adonitol; mannitol; 2,5-dipropyl-1,4-phenyldipropanol; 1,3-cyclopropanol; 2-propenyl-1,4-cyclohexane dipropanol; trimethylol propane; sorbitol; penacol; 2-methyl-1,4-cyclohexane dicarbinol; 3-isopropoxy-1,4-cyclohexane dipropanol; 2-ethenyl-1,3-cyclopentane dicarbinol; 1,4-phenyldicarbinol; 2-propyl-1,4-phenyldiethanol; 3-butoxy-1,4-phenyldibutanol; and the like. The preparation of the above polyols is known to the art in Acta Pharm. Jugaslav. Vol 2 pages 134 to 139, 1952; Ann. Vol. 594, pages 76 to 88, 1955; J. Am. Chem. Soc. Vol 71, pages 3618 to 3621, 1949; ibid., Vol. 74, pages 2674 to 2675, 1952; Chem. Abst., Vol. 42, pages 8774 to 8775, 1948; ibid., Vol 43 pages 571 to 573 and 6652, 1949; ibid., Vol. 44, pages 2554 and 7231, 1950; ibid., Vol. 46, page 9585, 1952; ibid., Vol. 47, page 7575, 1953; ibid., Vol. 48, page 106, 1954, ibid., Vol. 49, pages 6098 to 6099, 1955; Encyclopedia of Chemical Technology, Kirk-Othmer, Vol. 10, pages 638 to 678, 1966, published by Interscience Publishers, New York.

Also, phenolic polyols (two or more phenolic hydroxyl groups) and mixed phenolic-alcoholic polyols may be employed. Also mixtures of two or more polyols may be employed. Examples of polyols and of mixed phenolic-alcoholic polyols are as follows:
4,4'-isopropylidenediphenol (bisphenol A);
4-hydroxybenzylalcohol;
4-hydroxy-3-methoxybenzylalcohol;
p-hydroxyphenethylalcohol;
4,4'-dihydroxydiphenyl;
4,4'-dihydroxydiphenylmethane;
2,4-dihydroxybenzaldehyde; catechol; resorcinol; hydroquinone;
2,2'-dihydroxybenzophenone;
2,4-dihydroxybenzophenone; and
3,4-dihydroxymethylcinnamate; also
non-phenolic polyols having aromatic linking groups between the hydroxyl groups, e.g. 1,4-dihydroxymethylbenzene. Furthermore, tri- (and higher) hydric phenols may be used such as pyrogallol; hydroxyhydroquinone; phloruglucinol; and propyl gallate.

The following specific examples will serve further to illustrate the practice of the invention. Table I immediately following identifies the ketene acetals of the Examples (Compounds I through XII) and it also identifies ketene acetals of a sub-group of Type I which may be used.

Compounds XI and XII and methods of preparation are as follows:

EXAMPLE 1

10.00 grams (0.0543 moles) of Compound I and 6.40 grams (0.0543 moles) of 1,6-hexanediol were weighed into a 200 ml 3-necked, paddle stirred flask under rigorously anhydrous conditions. The anhydrous conditions were maintained while 50 ml of dried tetrahydrofuran was added to the flask and the stirrer activated. After a very brief induction period, the reaction mixture spontaneously warmed up to 43° C. and then gradually returned to room temperature. After stirring at room temperature for about one hour the high molecular weight poly (ortho ester) was isolated by either precipitation into n-hexane which contained a small amount of triethylamine followed by filtration of the white solid, or by evaporation of the tetrahydrofuran in a Teflon coated pan placed in a vacuum chamber.

The polymer had the following structure

Figure 1:
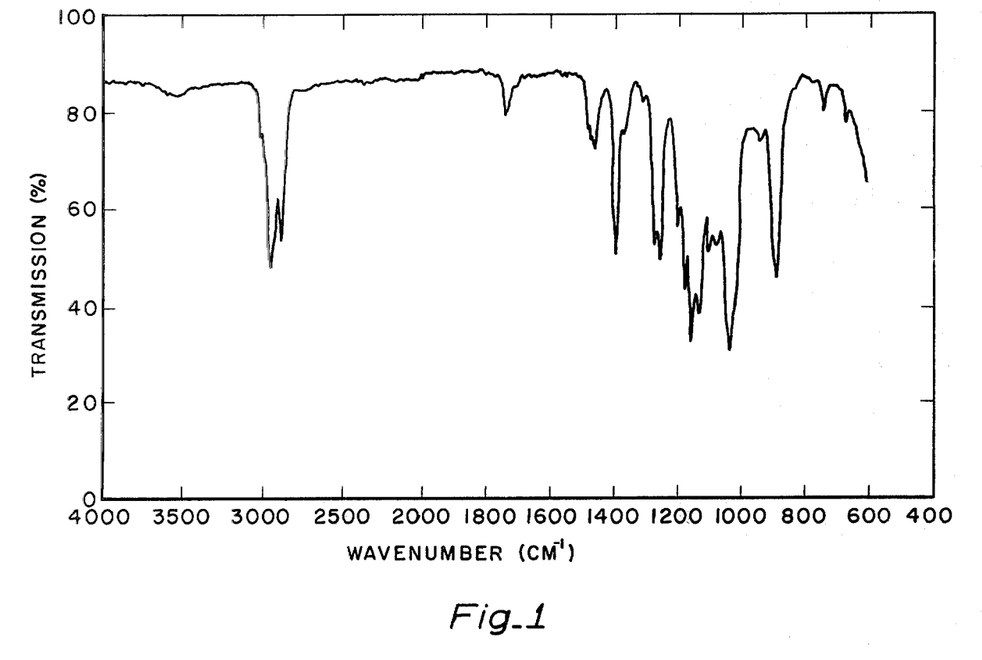
Figure 2:
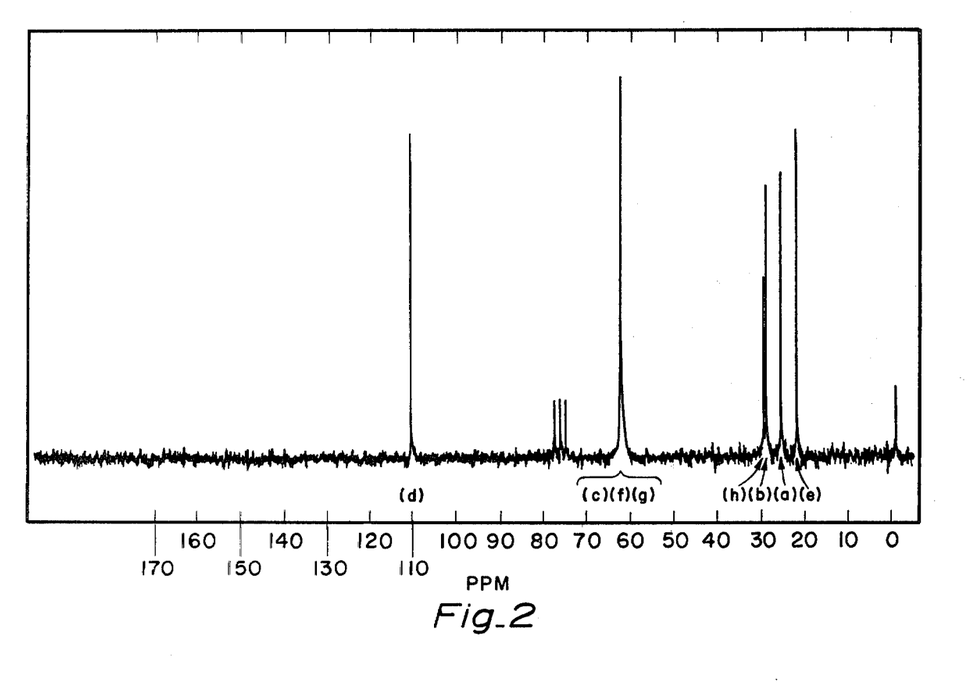

The infrared spectrum is shown in FIG. 1 and the $C^{13}$ NMR spectrum in FIG. 2. The weight average molecular weight obtained by light scattering was 166,000 and the polydispersity obtained from gel permeation chromatography 1.52. The degree of polymerization, n, was 335.

EXAMPLE 2-5

Following the procedure of Example 1, but replacing 1,6-hexanediol with: trans-1,4-cyclohexane dicarbinol; 1,2-propanediol; ethylene glycol; 2-methyl- 1,3-propanediol, the following polymers are formed:

EXAMPLE 6

Using the same conditions as in Example 1, 15.00 grams (0.0781 moles) of compound II and 9.22 grams (0.0781 moles) of 1,6-hexanediol are dissolved in 90 ml of tetrahydrofuran and 3 ml of a solution containing $1 \times 10^{-6}$ moles of iodine per ml of pyridine are added. There is an immediate temperature rise to 52° C. after which it gradually returns to room temperature. After stirring at room temperature for about one hour, the polymer is isolated as described in Example 1, and has the following structure where n is 10 to 1000.

EXAMPLE 7

Using the same conditions as in Example 1, 42.00 grams (0.1567 moles) of Compound V and 14.10 grams

(0.1567 moles) of 1,4-butanediol are dissolved in 200 ml of 1,2-dimethoxyethane and 1 ml of solution containing $1 \times 10^{-4}$ mole of p-toluenesulfunic acid monohydrate per ml of tetrahydrofuran is added. After the slight temperature rise subsides, the mixture is stirred at room temperature for about one hour and the polymer is isolated as described in Example 1. The polymer has the following structure where $\overline{M}_w$ is 196,000 and the $\overline{M}_w/\overline{M}_n$ is 1.48.

The polymer has the following structure.

EXAMPLE 8

Repeating the procedure of Example 7, but replacing Compound V and 1,4-butanediol with 40.00 grams (0.1667 mole) of Compound VI and 19.67 grams (0.1667 mole) of 1,6-hexanediol, the following polymer is obtained.

EXAMPLE 9

Repeating the procedure of Example 6, but replacing Compound II and 1,6-hexanediol with 12.00 grams (0.0652 moles) of Compound I and 7.43 grams (0.0652 moles) of trans-1,4-cyclohexanediol, the following polymer is obtained:

EXAMPLE 10

Repeating the procedure of Example 6, but replacing Compound II and 1,6-hexanediol with 35.00 grams (0.1768 moles) of Compound III and 25.11 grams (0.1768 moles) of trans-1,4-cyclohexanedicarbinol, the following polymer is obtained.

EXAMPLE 11

Repeating the procedure of Example 6, but replacing Compound II and 1,6-hexanediol with 25.00 grams (0.1437 moles) of Compound VII and 20.41 grams (0.1437 moles) of trans-1,4-cyclohexanedicarbinol, the following polymer is obtained:

EXAMPLE 12

Repeating the procedure of Example 6, but replacing Compound II and 1,6-hexanediol with 30.00 grams (0.0673 moles) of Compound VIII and 6.06 grams (0.0673 moles) of 1,4-butanediol, the following polymer is obtained:

EXAMPLE 13

Repeating the procedure of Example 6, but replacing Compound II with 28.00 grams (0.1228 moles) of Compound IX and using 14.49 grams (0.1228 moles) of 1,6-hexanediol, the following polymer is obtained:

EXAMPLE 14

Repeating the procedure of Example 7, but replacing Compound V and 1,4-butanediol with 30.00 grams (0.1220 moles) of Compound X and 9.27 grams (0.1220 moles) of 1,2-propanediol, the following polymer is obtained.

EXAMPLE 15

Repeating the procedure of Example 1 but employing a mixture (0.02715 moles each) of 1,6-hexanediol and trans-1,4-cyclohexane dicarbinol, the following polymer is obtained:

The two diol residues are randomly located in the chain and are shown as alternating merely for convenience.

EXAMPLE 16

Repeating the procedure of Example 6, but replacing Compound II and 1,6-hexanediol with a mixture of 7.00 grams (0.0380 moles) of Compound I and 7.30 grams (0.0380 moles) of Compound II and 4.71 grams (0.0760 moles) of ethylene glycol, the following polymer is obtained:

Similarly the groups derived from the two diketene acetals are randomly located.

EXAMPLE 17

Repeating the procedure of Example 6, but replacing Compound II and 1,6-hexanediol with 25.00 grams (0.1359 moles) of Compound I and 30.98 grams (0.1359 moles) of bisphehol-A, the following polymer is obtained.

EXAMPLE 18

The procedure of Example 7 is repeated except that no solvent is used and instead the reaction mixture is heated to 70° C. in order to achieve a homogeneous solution. Compound V and 1,4-butanediol used in Example 7 are replaced with 33.06 grams (0.1333 moles) of compound IV and a mixture of 9.60 grams (0.1000 moles) grams 1,4-butanediol and 5.39 grams (p.0333 moles) of 1,2,6-hexanetriol. The following crosslinked polymer is obtained:

As in the case of Examples 15 and 16, the residues of the diol and the triol are randomly located. The joint use of a diol and a triol enables one to control the density of crosslinking.

EXAMPLE 19

The procedure of Example 6 is repeated except that no solvent is used and instead the reaction mixture is heated to 65° C. in order to achieve a homogeneous solution. Compound II and 1,6-hexanediol used in Example 6 are replaced with 25.00 grams (0.1263 moles) of Compound III and 16.92 grams (0.1263 moles) of trimethylolpropane. The following cross-linked polymer is obtained:

In Examples 18 and 19 the pendant valence bonds indicate crosslinking to similar chains.

EXAMPLE 20

The procedure of Example 6 is repeated except that no solvent is used and instead the mixture is heated to 60° C. in order to achieve a homogeneous solution. Compound II and 1,6-hexanediol are replaced with 10.00 grams (0.0794 moles) of Compound XI and 7.38 grams (0.1191 moles) of ethylene glycol. The following polymer is obtained:

EXAMPLE 21

The procedure of Example 6 is repeated except that no solvent is used and instead the mixture is heated to 85° C. in order to achieve homogeneous solution. Compound II and 1,6-hexanediol are replaced with 15.00 grams (0.0490 moles) of Compound XII and 6.62 grams (0.0731 moles) of 1,4-butanediol. The following polymer is obtained:

The following example is illustrative of the use of the polymers of this invention as carriers or matrices for a drug.

EXAMPLE 22

Delivery devices were prepared by putting 7.2 grams of the polymer of Example 1 on a Teflon coated pan heated to a surface temperature of about 150° C. to provide a melt consistency permitting mixing to produce a thorough dispersion of 0.8 grams of micronized $Na_2CO_3$ and 2.0 grams of micronized norethindrone into the polymer melt. Sheets of the polymer mixture 20 mil and 40 mil in thickness 3"×3" square were pressed at 135° C. (275° F.), and 10,000 psi between sheets of Teflon covered foil using the appropriate thickness mold spacers. ¼" discs were punched from these sheets. These discs are suitable as implants.

Alternatively, the drug may be incorporated in the mixture of monomers before polymerization. In the case of crosslinked polymers such as those of Examples 18 to 21 this will be done because the polymers are infusible and insoluble in solvents.

The same procedure may be employed with any of the polymers of the present invention such as those of Example 2 to 21.

Other drugs may be similarly incorporated in the polymers of the invention. Among others these drugs or beneficial agents may include any of those mentioned in Choi and Heller U.S. Pat. No. 4,093,709 column 29, line 45 to column 30, line 37; also insecticides and other biologically active agents.

Examples 18 and 19 illustrate the use of polyols having a functionality greater than two and Examples 20 and 21 illustrate the use of ketene acetals having a functionality greater than two. As stated above, where crosslinking is desired, it is preferred to use tri- and higher functionality polyols because of their greater availability. Mixtures of polyols of different functionality, e.g. 2 and 3 and/or mixtures of ketene acetals of different functionality, e.g. 2 and 3 may be used. By using, for example, a mixture of diol and triol the density of crosslinking can be controlled by the ratio of diol to triol.

As noted above, a sub-group of Type I polymers are derived from ketene acetals of the formula:

That is, the grouping (R) may contain no single radical as in Compound I to which all four of the interior acetal oxygen atoms are attached. Examples of such Type I ketene acetals and resulting polymers are as follows:

TABLE II

Compound XIII

Compound XIV

Compound XV

Compound XVI

Compound XVII

Compound XVIII

The corresponding polymers are as follows, in which R represents the polyol residue:

| Ketene Acetal | Polymer |
|---|---|
| XIII | |
| XIV | |
| XV | |
| XVI | |
| XVII | |
| XVIII | |

It will be understood that crosslinked polymers of Compounds XIII through XVII may be produced by using tri- and higher functionality polyols, and/or by using ketene acetals of tri- or higher functionality.

Among the advantages of my novel polymers are the following: Being prepared by a reaction between a ketene acetal and polyol, they do not require removal by heat and distillation of small molecules. Also, the reaction proceeds to a high degree of polymerization at low temperature. Therefore, a drug, even one that is sensitive to elevated temperatures, can be incorporated in the mixture of monomers and will appear in the polymer without degradation. This is especially advantageous in the case of crosslinked polymers. These are infusible and insoluble, and therefore are not susceptible to incorporation of a drug after the polymerization process is complete, but this disadvantage is overcome by adding the drug to the mixture of monomers and carrying out the reaction, if need be, in a mold which molds the polymer with the drug incorporated to the desired shape and size as it is formed. Also, the polymer structure is pure and the finished product does not contain unreacted monomer.

It will be apparent from the specific examples that the reactions of ketene acetals with polyols are facile. They proceed at room temperature and being exothermic, they are allowed to rise in temperature as the reaction proceeds to completion. Suitable solvents are polar aprotic solvents, e.g. glyme, diglyme, dimethylacetamide, dimethyl sulfoxide, dimethylformamide, acetonitrile, pyrrolidone, and methylbutyl ether. When crosslinking occurs, solvents are not used. Catalysts are not required but when used, suitable catalysts are iodine in pyridine, p-toluensulfonic acid; also Lewis acids such as boron trichloride, boron trifluoride, boron trichloride etherate, boron trifluoride etherate, stannic oxychloride, phosphorous oxychloride, zinc chloride, phosphorous pentachloride, antimony pentafluoride, stannous octoate, stannic chloride, diethylzinc, and mixtures thereof; also, Bronsted catalysts in addition to p-toluene sulfonic acid such as poly-phosphoric acid, crosslinked polystyrene sulfonic acid, acidic silica gel, and mixtures thereof. The amount of catalyst used may be about one part catalyst to about 500 parts of the ketene acetal monomer. Smaller or larger amounts can also be used, such as 0.005% to about 2.0% based on the weight of the starting monomer.

Referring to the Type I and Type II polymers, there are various organic groups such as those in the R—O— groups, those forming parts of pendant groups such as those forming linking groups or parts of linking groups such as (R) and and the polyol residue $\underline{R}$. Referring to these groups collectively as "R groups", the following observations are in order: In some instances, the "R groups" may be hydrogen. Where they are not hydrogen, they are essentially hydrocarbon groups as defined above; i.e., they do not exclude groups containing hetero atoms provided the presence of the hetero atom or atoms is not incompatible with the intended use and with bioerodibility, and do not give rise to toxic or non-metabolizable degradation products. An instance of such permissible groups containing hetero atoms is the case where $\underline{R}$ (the polyol residue) is derived from a polymer of an alkylene oxide (e.g. ethylene oxide, propylene oxide, butylene oxide, tetrahydrofuran and the like) in which case $\underline{R}$ has the formula in which X is 1, 2 or 3, R is hydrogen or alkyl, and n is an integer equal to one or more. Another case is that of hydroxy terminated polyesters represented by the general formula in which case R is represented by the formula wherein a and b are positive integers. Examples of such polyesters are the glycolides and lactides.

The "R groups" as defined above may be of low molecular weight, e.g. methyl, ethyl, $-CH_2-CH_2-$, etc., or they may be of high or intermediate molecular weight. Practical considerations will influence the choice of molecular weight. For example, "R groups" of high molecular weight which are pendant groups, or which form linking groups or parts of linking groups, or are parts of R—O— groups, or which are derived from high molecular weight polyols, may be available only from expensive starting materials, or may impart less desirable characteristics to the polymer.

We claim:

1. Polymers of polyols and ketene acetals having a functionality of two or more.

2. Polymers according to claim 1 wherein the polyol and/or the ketene acetal has a functionality greater than two and the resulting polymer is crosslinked.

3. Polymers according to claim 2 wherein at least some of the polyol reactant has a functionality greater than two.

4. Polymers according to claim 3 wherein the polyol reactant is a mixture of a diol and a polyol having a functionality greater than two.

5. Polymers according to claim 2 wherein the ketene acetal has a functionality greater than two.

6. Linear polymers according to claim 1 wherein both the polyol and the ketene acetal have a functionality of two.

7. Polymers having the repeating mer unit:

wherein n is an integer substantially greater than 10; wherein $R_1$ and $R_2$ are hydrogen or the same or different essentially hydrocarbon groups and may be separate groups or may form parts of a cyclic group; Ⓡ is a quadrivalent organic grouping; $R_3$ and $R_4$ are hydrogen or the same or different essentially hydrocarbon groups and may be separate groups or may form parts of a cyclic group; $R_5$ is an essentially hydrocarbon group which is the residue of a polyol $R_5(OH)_a$ wherein a is an integer equal to two or more, such polyol being a single molecular species or a mixture of molecular species; and wherein such linear chain may be crosslinked with other similar chains.

8. Polymers according to claim 7 wherein Ⓡ is a single quadrivalent radical attached to all of the interior acetal-forming oxygen atoms.

9. Polymers according to claim 8 wherein Ⓡ is a spiro structure.

10. Polymers according to claim 8 wherein Ⓡ is an open chain aliphatic group.

11. Polymers according to claim 8 wherein Ⓡ contains a carbocyclic group.

12. Polymers according to claim 7 wherein $R_5$ in at least some of the mer units is alkylene or contains a carbocyclic group.

13. Polymers according to claim 7 wherein $R_5$ in at least some of the mer units is derived from a polyol of greater functionality than three and the polymers are crosslinked.

14. Polymers according to claim 13 wherein some of the $R_5$'s are derived from diols and others are derived from polyols of greater functionality.

15. Polymers having the repeating mer unit wherein n is an integer substantially greater than 10; wherein $R_1$, $R_2$, $R_3$ and $R_4$ are the same or different essentially hydrocarbon groups, $R_1$ and $R_2$ being separate groups or parts of a cyclic group and $R_3$ and $R_4$ being separate groups or parts of a cyclic group; $R_5$ is an essentially hydrocarbon group which is the residue of a polyol $R_5(OH)_a$ wherein a is an integer equal to two or more, such polyol being a single molecular species or a mixture of molecular species; $R_6$ is a valence bond or an essentially hydrocarbon group; $R_7$ and $R_8$ are hydrogen or essentially hydrocarbon groups which may be separate groups or may form parts of a cyclic group; and wherein such linear chains may be crosslinked to similar chains.

16. Polymers according to claim 15 wherein the group is selected from the class consisting of alkylene and groups containing a carbocylic ring.

17. Polymers according to claim 15 wherein $R_5$ in at least some of the mer units is alkylene or contains a carbocyclic group.

18. Polymers according to claim 15 wherein $R_5$ in at least some of the mer units is derived from a polyol having a greater functionality than three and the polymers are crosslinked.

19. Polymers according to claim 18 wherein some of the $R_5$'s are derived from diols and others are derived from polyols of greater functionality.

20. A method of producing poly (ortho esters) which comprises polymerizing a mixture of a polyol and a ketene acetal having a functionality greater than one.

21. The method of claim 20 wherein the polymerization is carried out at a temperature not greatly in excess of the temperature to which the reaction mixture rises by reason of the heat of reaction.

22. The method of claim 20 wherein the reaction is carried out in the substantial absence of a solvent.

23. The method of claim 20 wherein a beneficial agent is incorporated in the mixture of monomers before they are polymerized.

24. The method of claim 23 wherein at least one of the monomers has a functionality greater than two and the resulting polymer is crosslinked.

25. Polymers of claim 1 in admixture with biologically active agents.

26. Polymers of claim 7 in admixture with biologically active agents.

27. Polymers of claim 15 in admixture with biologically active agents.

28. Polymers of claim 25 in shaped form fitted for end use.

29. Polymers of claim 26 in shaped form fitted for end use.

30. Polymers of claim 27 in shaped form fitted for end use.

* * * * *